{ US005818467A }

United States Patent [19]

Schimitzek

[11] Patent Number: 5,818,467
[45] Date of Patent: Oct. 6, 1998

[54] DEVICE FOR INTEGRATING DIAGNOSTIC IMAGING AND DATA-PROCESSING DEVICES SYSTEMS INTO EDP SYSTEMS

[75] Inventor: Peter Schimitzek, Geilenkirchen, Germany

[73] Assignee: CSB-System Software-Entwicklung & Unternehmensberatung GmbH, Geilenkirchen, Germany

[21] Appl. No.: 628,740

[22] PCT Filed: Sep. 23, 1994

[86] PCT No.: PCT/DE94/01124

§ 371 Date: Apr. 8, 1996

§ 102(e) Date: Apr. 8, 1996

[87] PCT Pub. No.: WO95/10816

PCT Pub. Date: Apr. 20, 1995

[30] Foreign Application Priority Data

Oct. 13, 1993 [DE] Germany .......................... 43 34 782.7
May 5, 1994 [DE] Germany .......................... 44 15 818.1

[51] Int. Cl.⁶ ................................................... G06F 15/00
[52] U.S. Cl. ............................................................ 345/520
[58] Field of Search ................................... 345/520, 501, 345/522, 526

[56] References Cited

U.S. PATENT DOCUMENTS 5,208,745  5/1993  Quentin et al. ........................ 364/188

FOREIGN PATENT DOCUMENTS 3533336  9/1985  Germany .
3534065  9/1985  Germany .
2 246 456  1/1992  United Kingdom .

OTHER PUBLICATIONS

Franchi, "Multimedia Perspectives for the Next Generation PAC System", IEEE, 1992, pp. 156–169.
Barbosa et al. "Multimedia Services and Applications" EU Trans. on Telecommunications & Related Tech., Feb. 1991, pp. 5–19.

*Primary Examiner*—Phu K. Nguyen
*Attorney, Agent, or Firm*—Michael J. Striker

[57] ABSTRACT

The device for integrating diagnostic imaging and data processing devices into an EDP system records and transmits image, sound and text data and prints, files and analyzes it. It is connected to at least one examination system (22) which can be interfaced to it with an analog or digital interface and includes a main personal computer (3) with a dedicated interface board for a printer (4), an additional module (18) for a frame grabber board, an additional foot switch (19), a dedicated interface board in the printer (4) for a printer (20), a special automatic control system (21), a dedicated terminal in the personal computer for high-speed networks (23), a trigger system (24) and an audio recording device (27) and audio replay device (28) connected to the main personal computer (3). A network card (7) for network personal computers (8,9,10) can be connected to the main personal computer (3) so that authorized individuals can access the stored data.

7 Claims, 1 Drawing Sheet

DEVICE FOR INTEGRATING DIAGNOSTIC IMAGING AND DATA-PROCESSING DEVICES SYSTEMS INTO EDP SYSTEMS

BACKGROUND OF THE INVENTION

The invention relates to a device for the integration of diagnostic image-generating and data processing devices into EDP systems, by means of which it is possible to make video, audio and text data recordings and transmissions and to print, file and analyze data.

A invention is disclosed in patent publication DE-OS 35 33 446, whereby a medical video archive was created, by means of which it is easily and rapidly possible to study reference images and also clinical images. In addition, there is a device in which the required data can be stored, and a further device for inputting retrieved data in accordance with the desired reference image and clinical image is provided. A device for the retrieval of at least one image from the stored images, as well as for controlling the memory device, the input device, the retrieval device and the display device in such a way that one or several reference images and clinical images are retrieved from the reference images and clinical images stored in the memory device, so that the retrieved reference images and clinical images are displayed is provided.

A picture archive is represented in patent publication DE-OS 35 33 466, wherein a reproducing method for reproducing an already recorded picture and a first recording method for recording video signals is provided, while the picture provided by the picture recording device is continuously displayed on a display unit, a second recording device is provided wherein immediately following the recording of a video signal on a video plate the just recorded video signal is automatically read and is played on the display unit for a predetermined length of time. Then the just recorded picture is displayed on the display unit in order to start the recording process of the next picture. This makes it possible to determine easily and rapidly whether or not the recorded picture was correctly recorded.

A storage system for images from the medical field is furthermore known from German Published Patent Application DE-OS 35 34 065, which comprises a video data memory section, a video input and output section for the input/output of the video data, a retrieval section for storing the video data in the memory section and for retrieving them from it on the basis of retrieval data, a retrieval data input section for the input of the retrieval data into the retrieval section and a retrieval data section for storing the retrieval data, wherein the retrieval data are classified by means of an information block obtained during individual examination.

If images from the medical field are stored, retrieval data which have been collected for each examination are used for reducing the amount of retrieval data, while during reproduction the retrieval is performed for each individual examination, because of which the time required for retrieval is reduced.

All above-mentioned solutions have the disadvantage that they are not designed for multi-media. Video, audio and text signals are not capable of being integrated. The simultaneous digital display of the data next to an analog display is also not provided. These above-mentioned systems also have the disadvantage that they do not integrate heterogeneous systems, i.e. the doctor is not placed in a position where he can collect the various signals and is not offered the option by means of the hardware to transfer them to the digital system.

SUMMARY OF THE INVENTION

To remove the above-mentioned disadvantages of the prior art, it is the object of the invention to develop a device for the integration of diagnostic image-generating and data processing devices for EDP systems, which integrates a heterogeneous system, contains a system designed for multimedia and wherein video, audio and text signals are capable of being integrated.

According to the invention, the device for integration of diagnostic image-generating and data processing devices into an EDP system comprises a digital integration system including means for connection to one or more image-providing examination systems; a main personal computer equipped with a printer, a specially-produced printer interface card for the printer, an additional module for a frame grabber card, an additional foot switch, a specially built-in interface card in the printer, a special automatic control system in the video recorder, a mouse and a keyboard; a menu monitor, a video monitor, an optical disk, a video monitor, a video recorder, a drive assembly A, fixed plates C and D, memories F and G, an audio-recording device, an audio-replay device, a network card including means for electrical connection with at least one network PC and a trigger system all electrically connected with the main personal computer via information lines for data and control signals. The main personal computer includes a graphics card connected with the menu monitor. The additional module for the frame grabber card of the main personal computer is connected with the image-providing information systems, is provided with an input connection for receiving signals from the video recorder and is provided with an output connection for sending signals to the video monitor. The main personal computer is connected with the special automatic control system of the video recorder and via the specially produced interface card in the main personal computer with the specially built-in interface card in the printer with the printer. The main personal computer is connected with the optical disk, the drive assembly A, the fixed plates C and D, the memories F and G with respective information lines (i,k,l,m,n,o). The input connection of the video recorder with the main personal computer is in parallel with output connection to the video monitor from the main personal computer.

The advantages of the invention reside in that a direct on-line filing and an on-line printing option are provided. Furthermore, an intelligent image analysis with automated tool use on different image planes is made possible on the A/D converter. In addition, multi-functional hardware interfaces are provided for connecting any video, audio and text transmission unit.

Furthermore, this device is designed in a multi-media manner for all carrier systems and one skilled in the art is given the opportunity of collecting the information from the various systems, and the hardware is capable of transferring these signals to digital systems.

A standardization of the examination process is assured by means of these advantages and a model-based evaluation of the organ structures in the state of rest and in motion is provided. A trigger-controlled image storage is present at the same time. All authorized users simultaneously have all data at their disposal. Video, audio and text data can be relocated or requested in accordance with the protocol for high-speed networks. Filing already starts with the examination process.

The optical waveguide technology for image-connected telecommunication and tele-consultation is employed in this device. Besides text video and audio digitizing, signal reception and processing of moving images in color is also possible. Graphics-capable text and layout processing allows the graphic presentation, reproduction, output and documentation of test material.

This device is suitable to meet the modern challenge in the health field regarding a more effective organization of health care, but also of cost reduction in this field, and the qualitative control of medical performance.

A further advantage resides in that the flood of the mass of information in the medical field of today is collected by this device, linked together and selected, so that it is effectively usable in therapy. The specialized EDP knowledge required of the medically-oriented user is reduced to a minimum. The processes in the sense of information-technological management remain in the background without bothering the user. The reproducibility of the processes is assured and an easily comprehensible and simple-to-operate patient-oriented information management is provided.

BRIEF DESCRIPTION OF THE DRAWING

The objects, features and advantages of the present invention will now be illustrated in more detail by the following detailed description, reference being made to the accompanying drawing in which the sole figure is a block diagram of the device for integration of diagnostic image-generating and data processing devices according to the invention.

DESCRIPTION OF THE PREFERRED EMBODIMENT

Figure 1:
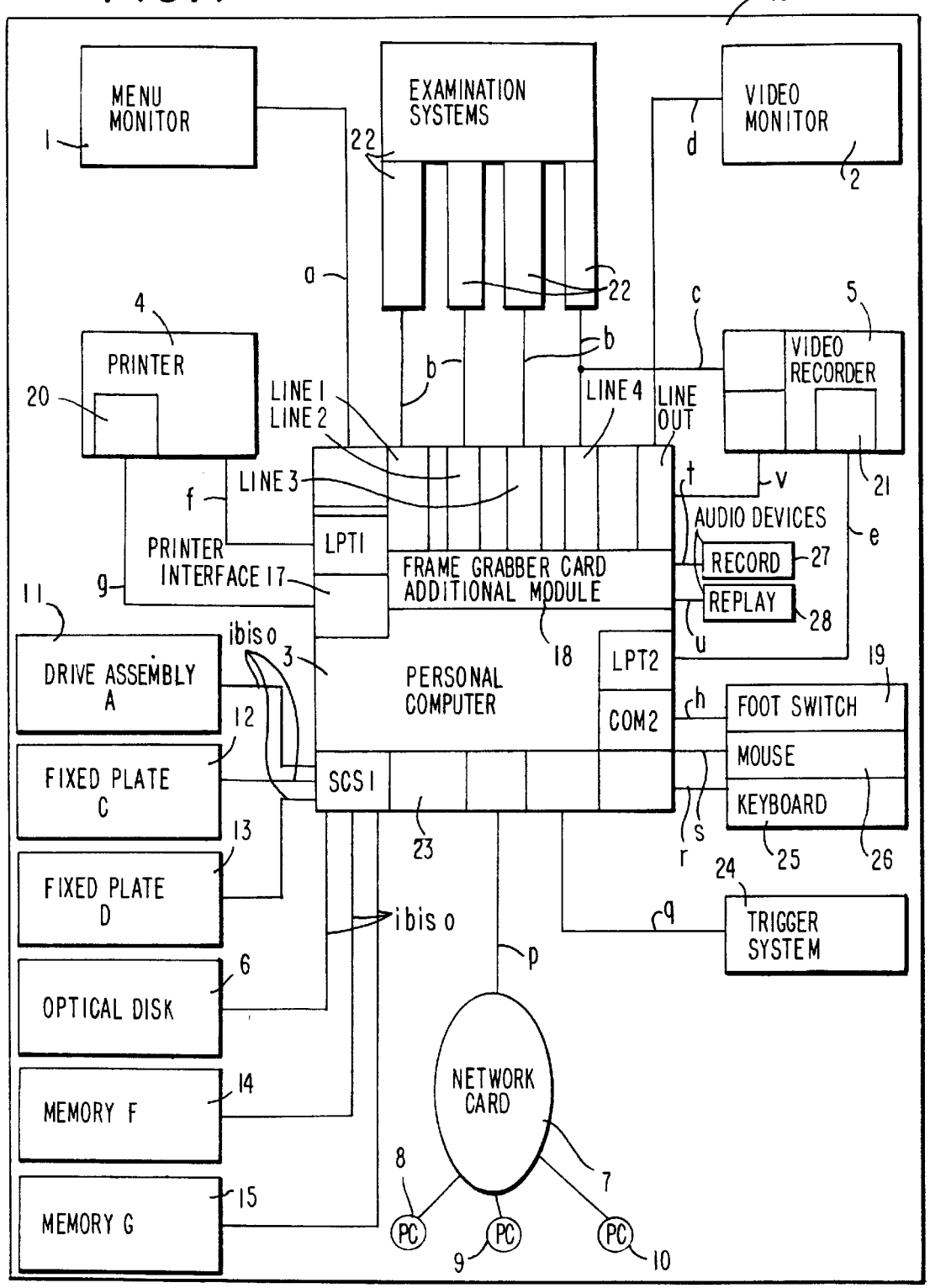

The device for the integration of diagnostic image-generating and data processing devices into EDP systems, to which each existing image-providing examination system can be connected and which consists of the menu monitor 1, the video monitor 2, the personal computer 3, the printer 4, the video recorder 5, the optical disk 6, the network 7 with network PCs 8, 9, 10, the drive assembly A 11, the fixed plates C and D 12, 13 and the memories F and G 14, 15, is characterized in that a digital integration system 16 of the personal computer 3, which, equipped with a specially-produced interface card in the personal computer 3 for the printer 17 and with an additional module for the frame grabber card 18, consists of an additional foot switch 19, of the printer 4 with a specially built-in interface card in the printer 4 for the printer 20, and of the video recorder 5 with a special automatic control system 21. The main personal computer 3 connected with its graphic card via the information line a with the monitor 1, with the additional module for the frame grabber card 18 via its LINE IN 1 to LINE IN 4, at least with one of these via the information lines b with the existing image-generating examination systems 22, at least via one of these with the additional module for the frame grabber card 18 via its LINE IN 1 to LINE IN 4 by means of the information line c with the LINE OUT of the video recorder 5, with the additional module for the frame grabber card 18 via its LINE OUT via the information line d with the video monitor 2, with its LTP2 via the information line e with the special automatic control system 21, with its LTP1 via the information line f with the printer 4, with is specially produced interface card in the personal computer 3 for the printer 17 via the information line g with the specially produced interface card in the printer 4 for the printer 20, with its COM2 via the information line h with the foot switch 19, via its SCS1 with the optical disk 6, the drive assembly A 11, the fixed plate C 12, the fixed plate D 13, the memory F 14 and the memory G 15 with their respective information lines i, k, l, m, n, o, is in operative connection with its net card via the information line p with the net 7 and via this with the PCs 8, 9, 10, by means of its connection for high-speed networks 23—specially installed in the the personal computer 3—via a separate line in accordance with the protocol instruction for these networks, with a trigger system 24 via the information line q, a keyboard 25 via the information line r and a mouse 26 via the information line s, as well as with an audio recording device 27 and audio-replay device 28 via the information line t or u, wherein the LINE IN of the video recorder 5 is switched parallel with the LINE OUT of the personal computer 3 and the video monitor 2 via the information line v.

The operation is as follows:

That, after the main personal computer 3 has been turned on, a corresponding operating system can be called up via the keyboard 25 or the mouse 26. Simultaneously therewith an image-providing examination system 22 or, if required, several image-providing examination systems 22 are displayed on the video monitor 2, wherein, if needed and required, there is the option of recording audio data (biosignals and/or comments of one skilled in the art) by means of an audio recording device 27 specially intended for this or via a network, and text data via the keyboard 25 or a network, which are temporarily stored in the memory of the personal computer together with and at the same time as the image-providing examination system or examination systems displayed on the video monitor 2. Subsequently the storage of the audio, video and/or text data in one of the positions of fixed plate D 13, memory F 14, memory G 15 is performed by means of operating the additional foot switch 19, or by means of operating the keyboard 25 or by means of operating the mouse 26. After this it is possible to recall the video, audio and text data as required by operating the additional foot switch 19 or the keyboard 25 or the mouse 26, so that the video, audio and text data are present in the personal computer 3, the image and, as required, the text appears on the video monitor 1 and possibly the image and, if required, the text can be viewed on the menu monitor 1 and the sound, if required, is present at the audio-replay device 28. It is furthermore possible, if required, that one or several images or pictures with text can be printed by means of the printer 4 in accordance with various arrangement criteria. Furthermore, recording and replay of stored video, text and audio data are possible via the video recorder 5 by operating the mouse 26 or the keyboard 25.

By including a network 7, the stored video, audio and text data are available to any authorized user via the respective network PCs 8, 9, 10.

By means of a provided connection, specially built into the main personal computer 3, for high-speed networks 23, conditions have been provided for this device to relocate or request these stored video, audio and text data in accordance with the protocol for high-speed networks.

A trigger system 24 has been furthermore assigned to the personal computer 3 and in this way makes a trigger-controlled image storage possible for this device.

Reference numerals used:
1. Menu monitor
2. Video monitor
3. Personal computer
4. Printer
5. Video recorder
6. Optical disk
7. Network
8. PCs
9. PCs
10. PCs
11. Drive assembly A
12. Fixed plate C
13. Fixed plate D
14. Memory F
15. Memory G
16. Digital integration system
17. Specially produced interface card in the personal computer 3 for the printer
18. Additional module for the frame grabber card
19. Foot switch
20. Specially built-in interface card in the printer 4 for the printer
21. Special automatic control system
22. Image-providing examination system
23. Connection for high-speed networks specially installed in the personal computer 3
24. Trigger system
25. Keyboard
26. Mouse
27. Audio recording device
28. Audio-replay device
a–v Information lines

I claim:

1. A device for integration of diagnostic image-generating and data processing devices into an EDP system, said device comprising a digital integration system (16) including means for connection of at least one image-providing examination system (22); a main personal computer (3) equipped with a printer (4), an additional module (18) for a frame grabber card, a mouse (26) and a keyboard (25); a menu monitor (1) connected with the main personal computer (3); a video monitor (2) connected with the main personal computer (3); an optical disk (6) connected with the main personal computer (3), a video monitor (2) connected with the main personal computer (3); a video recorder (5) connected with the main personal computer (3); a special automatic control system (21) in the video recorder (5); a drive assembly A (11) connected with the main personal computer (3); fixed plates C and D (12,13) connected with the main personal computer (3); memories F and G (14,15) connected with the main personal computer (3); an audio-recording device (27) connected with the main personal computer (3) via information line (t); an audio-replay device (28) connected with the main personal computer via information line (u); a network card (7) connected with the main personal computer via information line (p), said network card (7) including means for electrical connection with at least one network PC (8,9,10), and a trigger system (24) connected with the main personal computer (3) via information line (p);

wherein the main personal computer (3) includes a graphics card connected via information line (a) with the menu monitor (1), the additional module (18) for the frame grabber card of the main personal computer (3) is connected with the at least one image-providing information systems via information line (b), the additional module (18) for the frame grabber card of the main personal computer (3) is provided with an input connection for receiving signals from the video recorder (5) via information line (c), the additional module (18) for the frame grabber card of the main personal computer (3) is provided with an output connection for sending signals to the video monitor (2) via the information line (d), the main personal computer (3) is connected with the special automatic control system (21) of the video recorder (5) via an information line (e), the main personal computer (3) is connected with the printer (4) via an information line (f), the main personal computer (3) is connected with the foot switch (19) via an information line (h), the main personal computer (3) is connected with the optical disk (6), the drive assembly A (11), the fixed plate C (12), the fixed plate D (13), the memory F (14), the memory G (15) with respective information lines (i,k,l,m,n,o), and the input connection of the video recorder (5) with the main personal computer (3) is in parallel with output connection to the video monitor from the main personal computer (3) to allow the reception, processing, storage and reproduction of multimedia data.

2. The device as defined in claim 1, wherein the additional module (18) for the frame grabber card is provided with LINE IN terminals and a LINE OUT terminal and wherein at least one of the LINE IN terminals is connected with the at least one image-providing examination system (22) via said information line (b), the input connection to the video recorder (5) is a connection of the video recorder to at least one of the LINE IN terminals of the additional module (18) of the frame grabber card via said information line (c) and the output connection to the video monitor (2) of the additional module (18) is made to the LINE OUT terminal of the additional module (18) via said information line (d) to allow common viewing of analog and digital data.

3. The device as defined in claim 1, wherein the main personal computer (3) is provided with a high-speed network (23) including means for connection of a high-speed computer network and the main personal computer (3) is provided with means for controlling said networks according to protocol instructions for said networks to allow transfer of said multimedia data in real time to remote users.

4. The device as defined in claim 1, wherein the main personal computer (3) is provided with a specially produced printer interface card (17) for the printer (4) and the printer (4) has an integrated specially built-in interface card (20) and the printer (4) with the specially built-in interface card (20) is connected with the specially produced printer interface card (17) of the main personal computer (3), whereby simultaneous or delayed image-printing of at least one image is provided.

5. The device as defined in claim 1, wherein said additional foot switch (19) and said trigger system (24) includes means for trigger controlled image storing and a linking of said multimedia data.

6. The device as defined in claim 1, wherein at least one of said network PCs (8; 9; 10) is connected with the main personal computer (3) via said network card (7) to allow data transmission.

7. The device as defined in claim 1, wherein said audio-recording device (27) and said audio-replay device (28) include means for allowing additional use of audio data.

* * * * *